United States Patent

Kimura et al.

[11] Patent Number: 6,003,531
[45] Date of Patent: Dec. 21, 1999

[54] PIPETTE-WASHING DEVICE FOR AUTOMATIC BIOCHEMICAL ANALYZER

[75] Inventors: Akio Kimura; Shin Saito, both of Tokyo, Japan

[73] Assignee: JEOL Ltd., Tokyo, Japan

[21] Appl. No.: 08/915,924

[22] Filed: Aug. 21, 1997

[30] Foreign Application Priority Data

Aug. 21, 1996 [JP] Japan .................................. 8-219741

[51] Int. Cl.⁶ ...................................................... B08B 3/00
[52] U.S. Cl. ......................... 134/198; 134/170; 134/155; 134/201
[58] Field of Search .................................... 134/170, 140, 134/155, 186, 182, 183, 147, 148, 152, 198, 201; 422/100, 102

[56] References Cited

U.S. PATENT DOCUMENTS

| | | | |
|---|---|---|---|
| 4,018,240 | 4/1977 | Palthe | 134/196 |
| 4,127,137 | 11/1978 | Butcher | 134/174 |
| 4,200,607 | 4/1980 | Suzuki | 422/64 |
| 4,817,443 | 4/1989 | Champseix et al. | 73/864.22 |
| 4,820,497 | 4/1989 | Howell | 422/63 |
| 4,888,998 | 12/1989 | Buzza et al. | 73/865.21 |
| 4,948,563 | 8/1990 | Kanewske, III | 422/99 |
| 5,279,794 | 1/1994 | Sasao | 422/100 |

FOREIGN PATENT DOCUMENTS 5-2024  of 1993  Japan .

*Primary Examiner*—Frankie L. Stinson
*Assistant Examiner*—Paul J. Lee
*Attorney, Agent, or Firm*—Webb Ziesenheim Logsdon Orkin & Hanson, P.C.

[57] ABSTRACT

There is disclosed a pipette-washing device for use with an automatic biochemical analyzer. The pipette-washing device includes a wash fluid-ejecting block for ejecting a wash fluid toward pipette. An upwardly spreading groove is formed in the top surface of the body of the block and extends along the trajectory of the front end of the pipette. The groove is connected at its lower end with the vertical wash fluid channel. A lateral draining channel is formed in the body of the block and connected with the lower end of the vertical wash fluid channel. When the pipette moves, the front end of the pipette moves through the groove. The block is inclined at an angle to the vertical within a plane in which the groove extends.

7 Claims, 6 Drawing Sheets

PIPETTE-WASHING DEVICE FOR AUTOMATIC BIOCHEMICAL ANALYZER

FIELD OF THE INVENTION

The present invention relates to an automatic biochemical analyzer for analyzing biological samples such as blood and urine in terms of plural items and, more particularly, to a washing device for washing pipettes used to aspirate and discharge samples and reagents.

BACKGROUND OF THE INVENTION

Such automatic biochemical analyzers for analyzing biological samples have been known, as proposed in Japanese Patent Laid-Open No. 2024/1993. In this prior art technique, a plurality of sample containers are set on a sample disk. In this instrument, aliquots or sample in the sample containers set on the sample disk are drawn in by a sample pipette and dispensed into reaction containers on a reaction disk. A reagent pipette draws in reagents from plural reagent disks and adds the reagents to the aliquots of sample. Thus, the sample is analyzed in terms of plural items. During the analysis, the order in which the items are analyzed is determined, taking account of the time required for the processing, in order to shorten this processing time.

Where an aliquot of sample or reagent is injected by a pipette, a given amount of sample or reagent is aspirated while a portion of the pipette on the side of the front end is dipped in a sample or reagent held in a container. Then, the pipette is moved to a reaction container while the aliquot of sample or reagent is kept aspirated. Finally, the aliquot is injected into the reaction container. When the front end portion of the pipette is moved out of the container, a part of the aliquot of sample or reagent adheres to the outer surface of the front end portion of the pipette and remains there. Where a part of the aliquot of sample or reagent remains inside or outside the pipette in this way, if the next aliquot of sample or reagent is injected by the same pipette, various problems take place.

Accordingly, it is customary to wash the inner and outer surfaces of the pipette when the injection of one aliquot of sample or reagent ends. In the prior art technique, wash water is sprinkled on the outer surface to wash it. To wash the interior of the pipette, a given amount of wash water is drawn into the pipette, and then the drawn water is drained off.

However, if wash water is simply showered on the outer surface of the pipette, the wash water is not quickly discharged and thus a part of the wash water remains on the outer surface of the pipette. If a new sample is subsequently injected, the factor by which the sample is diluted may deviate from the intended value. If a reagent is aspirated, the concentration of the reagent may deviate from the intended value. Consequently, it is difficult to obtain accurate measurement results.

SUMMARY OF THE INVENTION

In view of the foregoing problem, the present invention has been made.

It is an object of the present invention to provide a pipette-washing device which is for use with an automatic biochemical analyzer and can wash a pipette in a minimum time with wash water that is drained away almost completely, whereby permitting more samples to be measured within a given period than heretofore.

This object is achieved in accordance with the teachings of the invention by a pipette-washing device for washing a pipette that aspirates a sample or reagent to be handled by an automatic biochemical analyzer and conveys the aspirated sample or reagent into another location, the pipette-washing device comprising: a wash fluid-ejecting block mounted under a passage through which the pipette having a front end moves, the wash fluid-ejecting block acting to eject a wash fluid toward the pipette; a wash fluid supply means for supplying the wash fluid to the wash fluid-ejecting block; and a valve for controlling the supply of the wash fluid from the wash fluid supply means to the wash fluid-ejecting block. The wash fluid-ejecting block comprises a body in the form of a block. The body is provided with a wash fluid channel extending vertically. The body has an opening in its top surface. The opening faces the front end of the pipette and is in communication with the wash fluid channel. The wash fluid channel is connected with the wash fluid supply means at the lower end of the block. The front end of the pipette describes a trajectory. An upwardly spreading groove is formed in the top surface of the body and extends along the trajectory of the front end of the pipette. A draining channel is formed in the body and opens into the atmosphere through one side wall of the body. The wash fluid channel is connected at its lower end with the draining channel. When the pipette moves, its front end passes through the groove. The block is inclined at an angle to the vertical within a plane in which the groove extends.

Other objects and features of the invention will appear in the course of the description thereof, which follows.

SUMMARY OF THE INVENTION

Figure 1:
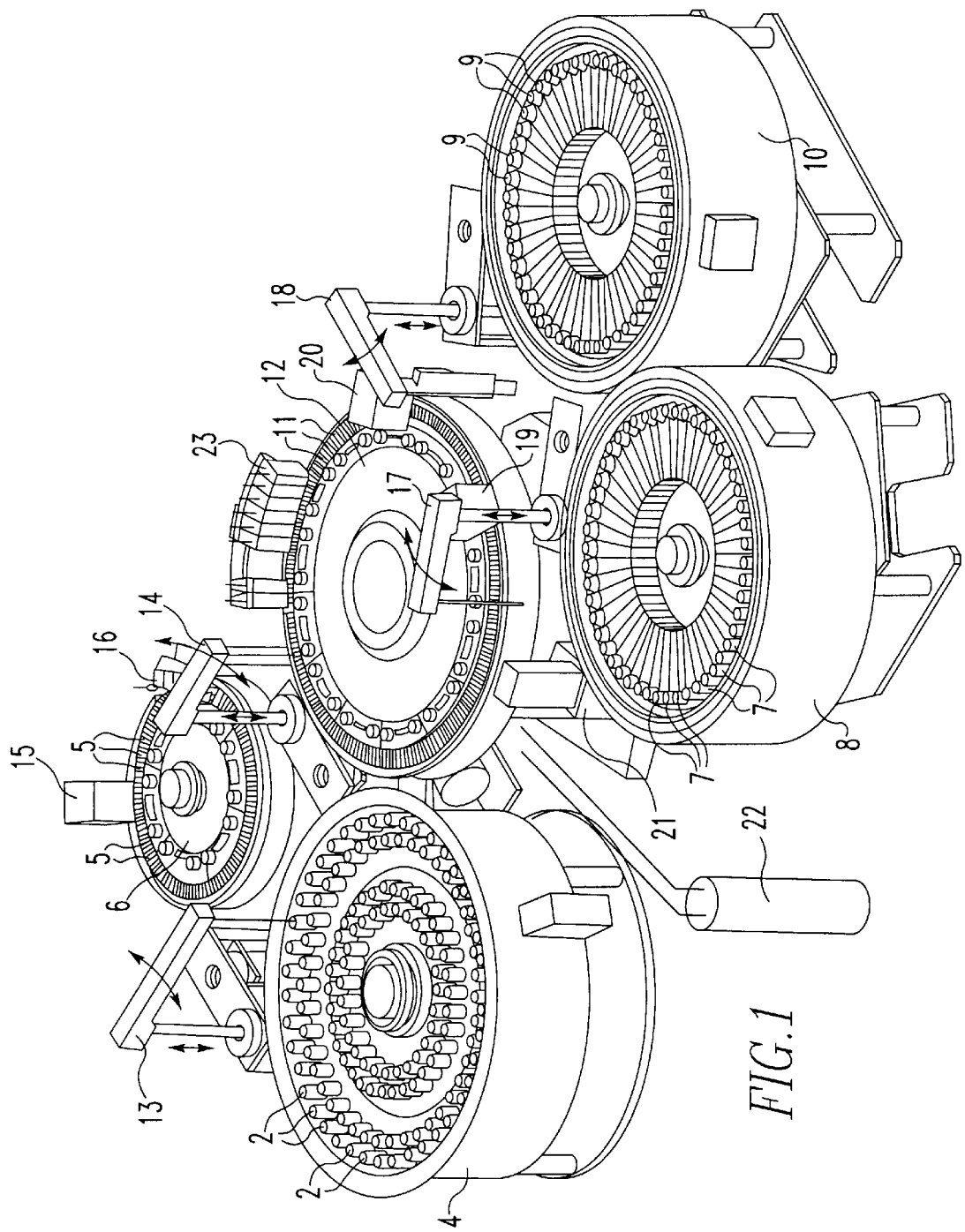
FIG. 1 is a perspective view of an automatic biochemical analyzer equipped with a pipette-washing device in accordance with the present invention, showing the whole construction of the analyzer.

The whole structure of an automatic biochemical analyzer in accordance with the present invention is shown in FIG. 1. The biochemical analyzer comprises a sample turntable 4, a diluting turntable 6, a first reagent turntable 8, a second reagent turntable 10, and a reaction turntable 12. A given number of sample containers 2 holding biological samples are set on the sample turntable 4. The samples are drawn from the sample containers 2 and diluted. The diluted samples are put in diluting containers 5, which in turn are set on the diluting turntable 6. Reagent containers 7 holding first and fourth reagents of different kinds are set on the reagent turntable 8. Reagent containers 9 holding second and third reagents of different kinds are set on the second reagent turntable 10. A given number of reaction containers 11 are set on the reaction turntable 12.

On the sample turntable 4, the sample containers 2 are arranged in two rows and regularly spaced from each other by one pitch. Each row consists of 42 sample containers 2. This sample turntable 4 is rotated incrementally, one pitch at a time.

A diluting pipette 13 is mounted between the sample turntable 4 and the diluting turntable 6 and reciprocated between the sample turntable 4 and the diluting turntable 6 by a drive mechanism (not shown). The diluting pipette 13 is moved up and down for aspirating and injecting operations. When the diluting pipette 13 gains access to one sample container 2 in a given location on the sample turntable 4, a sampling pump (not shown) is operated to take in a given amount of sample. Then, the diluting pipette 13 obtains access to one diluting container 5 in a given position on the diluting turntable 6. A given amount of diluent (normally physiological salt solution) supplied from the diluting pipette 13 itself is injected into the diluting container 5, along with the sample. As a result, the sample is diluted by a given factor within the diluting container 5. Thereafter, the diluting pipette 13 is washed by a washing device (not shown) located at the midway location in the reciprocating stroke of the pipette.

A sampling pipette 14, a stirring device 15, and a washing device 16 are mounted around the diluting turntable 6, as well as the diluting pipette 13. The diluted sample in the diluting container 5 is stirred by the stirring device 15, thus producing a uniform diluted sample. Let N be the number of the diluting containers 5 circumferentially arranged on the diluting turntable 6. The diluting turntable 6 is rotated incrementally, M pitches at a time. To arrange these devices 13, 14, 15, and 16 with sufficient degrees of freedom, M and N are so selected as not to have any common factor.

A drive mechanism (not shown) reciprocates the sampling pipette 14 between the diluting turntable 6 and the reaction turntable 12 through the pipette-washing device 16. When the sampling pipette 14 is lowered to gain access to one diluting container 5 in a given position on the diluting turntable 6, a diluting sampling pump (not shown) is operated to drawn in a given amount of diluted sample. Then, the sampling pipette 14 is lowered to obtain access to one reaction container 11 in a given position on the reaction turntable 12, and the pipette 14 injects the drawn diluted sample into the reaction container 11.

The stirring device 15 is moved up and down by a vertical driving mechanism (not shown) and has a stirring rod (not shown) reciprocating diametrically of the diluting turntable 6. The stirring rod of the diluting turntable 6 advances into a diluted sample in the diluting container 5 and moves back and forth to produce a uniform diluted sample. The washing device 16 cleanses the sampling pipette 14 after the diluted sample is injected into the reaction container 11.

Disposed around the reaction turntable 12 are reagent pipettes 17, 18, stirring devices 19, 20, a multi-wavelength photometer 21 acting as a detector, a thermostatic chamber 22, and a washing device 23 for washing the reaction container, as well as the sampling pipette 14. These devices operate at their respective positions relative to the reaction container 11.

Referring to FIG. 1, it is assumed that 221 reaction containers 11 are disposed along the whole outer periphery of the reaction turntable 12. Numerals 1 through 221 are given to 221 positions taken in a counterclockwise direction along the outer surface of the reaction turntable 12. A first reagent is injected at position 1. A fourth reagent is injected at position 2. The first reagent is stirred at position 4. The fourth reagent is stirred at position 5. A third reagent is injected at position 36. A second reagent is injected at position 37. The third reagent is stirred at position 39. The second reagent is stirred at position 40. The reaction container 11 is washed and checked for contamination at positions 80–107. A diluted sample is injected at position 113. The pipettes 14, 17, 18, the stirring devices 19, 20, and the washing device 23 perform their operations on the reaction container 11 halted at the positions described above.

The reagent pipette 17 is reciprocated between the reaction turntable 12 and the reagent turntable 8 by a driving mechanism (not shown). When the first reagent should be pipetted into the reaction container 11, the reagent pipette 17 is lowered and obtains access to the reagent container 7 located at a given position on the reagent turntable 8. Then, a reagent pump (not shown) is operated to draw in a given amount of reagent. Thereafter, the pipette rotates toward the reaction turntable 12. The pipette is lowered to get access to the reaction container 11 positioned at a given location on the reaction turntable 12. The drawn reagent is injected as the first reagent into the reaction container 11.

The reagent pipette 17 operates similarly when the fourth reagent held in other reagent container 7 is pipetted into the reaction container 11. As mentioned previously, the position at which the fourth reagent is pipetted differs from the position at which the first reagent is pipetted. That is, the reagent pipette 17 is designed so that it can come to a halt at two pipetting positions.

The stirring device 19 is moved up and down by a driving mechanism (not shown) and has a stirring rod (not shown) that is rotated and moved back and forth. The stirring rod is advanced into the reaction container 11 in a given position on the reaction turntable 12 and then rotated and moved back and forth diametrically of the reaction turntable 12. This assures that the first reagent induces a uniform reaction of the diluted sample.

The stirring device 19 similarly stirs the diluted sample and the fourth reagent inside the reaction container 11. As described above, the position at which the fourth reagent is stirred is different from the position at which the first reagent is stirred.

The reagent pipette 18 draws the second or third reagent from the second reagent turntable 10 and injects the drawn reagent into the reaction container located in a given position on the reaction turntable, in exactly the same way as the reagent pipette 17. The stirring device 20 stirs the second or third reagent and the diluted sample in the reaction container, in exactly the same manner as the stirring device 19.

The multi-wavelength photometer 21 measures the absorbance of the diluted sample inside the reaction container 11 and detects the reaction products arising from the diluted sample in the reaction container 11.

The thermostatic chamber 22 maintains constant the temperature of the reaction containers 11 on the reaction turntable 12 at all times.

The washing device 23 uses a draining pump (not shown) to draw in the detected diluted sample and reagent held in the reaction container 11. The drawn sample and reagent are discharged into a draining tank. Then, a wash fluid pump (not shown) supplies a wash fluid into this reaction container 11 to wash the interior of the reaction container 11. The wash fluid is then drawn off into the draining tank. At this time, the degree of contamination of the reaction container 11 is measured. If it is heavily contaminated, a warning is issued to replace the container.

Let N be the number of the reaction containers 11 circumferentially arranged on the reaction turntable 12. This reaction turntable 12 is rotated incrementally, M pitches at a time. To arrange these devices 14, 17, 18, 19, 20, 21, 22, and 23 with sufficient degrees of freedom, M and N are so selected as not to have any common factor. The reaction turntable 12 is rotated through more than 180 degrees in one step. In the present embodiment, the 221 reaction containers 11 are rotated in 112 pitches in one step.

Suppose that one reaction container is halted at a given position. This container is rotated in 112 pitches in the next one step and reaches position 113. The container is rotated in 112 pitches in the next one step and arrives at position 4. In summary, after incremental movements in two steps, the container has been moved in 3 pitches.

Figure 2:
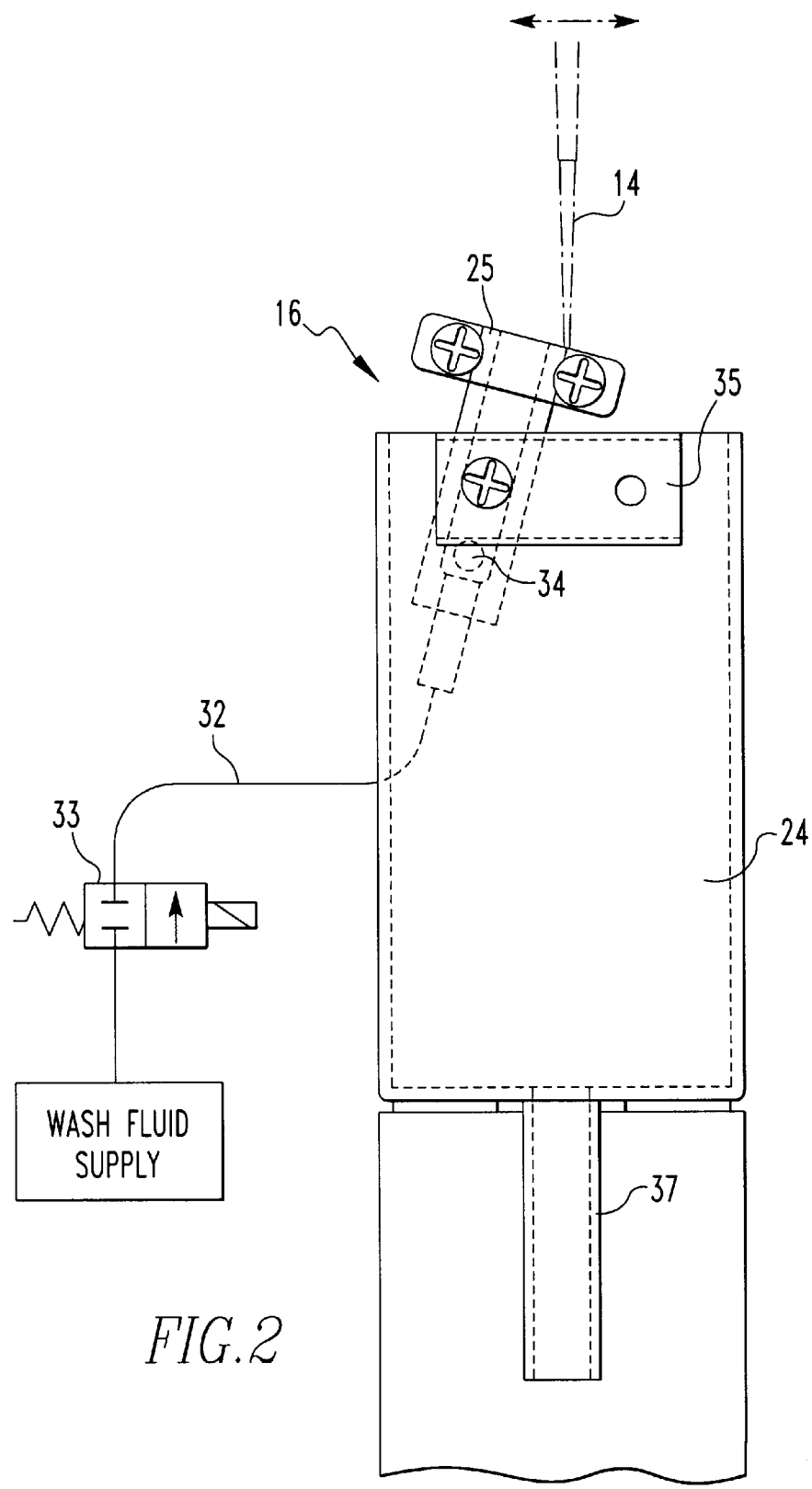
FIG. 2 is a front elevation of the pipette-washing device shown in FIG. 1.
Figure 3:
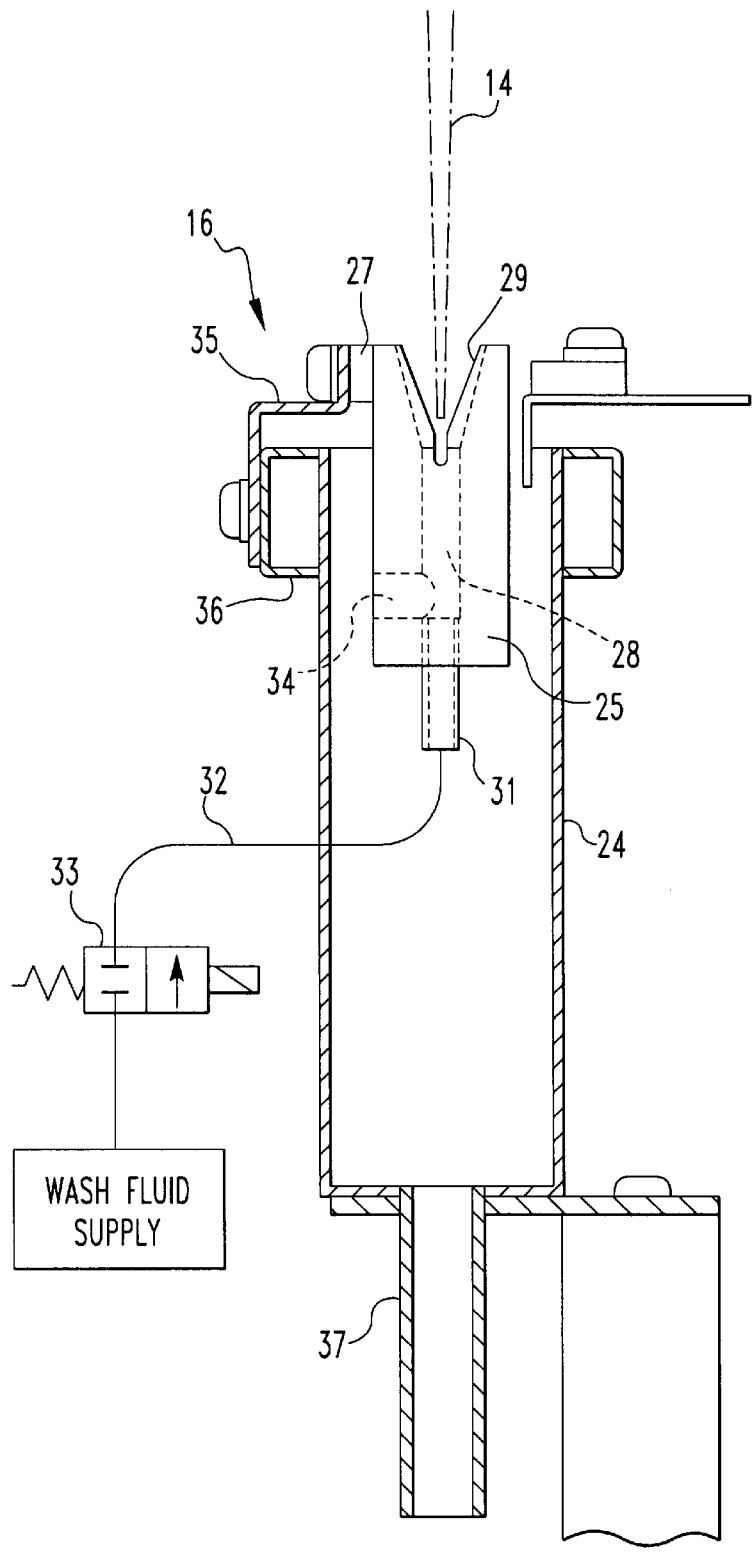
FIG. 3 is a side elevation partially in cross section of the pipette-washing device shown in FIG. 2.
Figure 4:
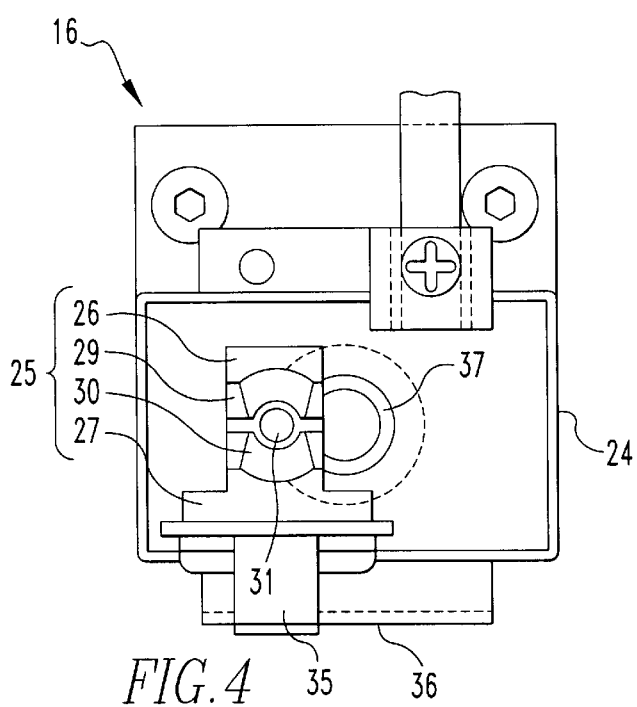
FIG. 4 is a plan view of the pipette-washing device shown in FIG. 2.
Figure 5B:
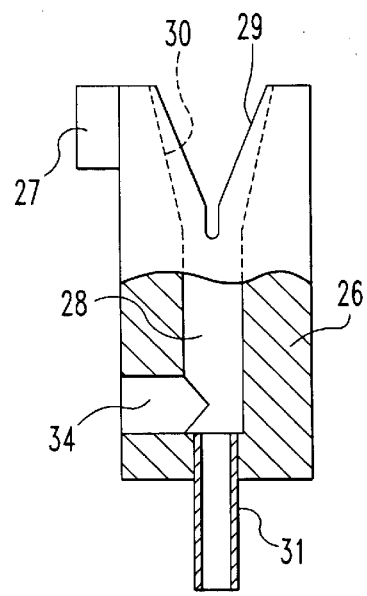
FIG. 5(b) is a left side elevation of the wash fluid-ejecting block shown in FIG. 5(a)
Figure 5A:
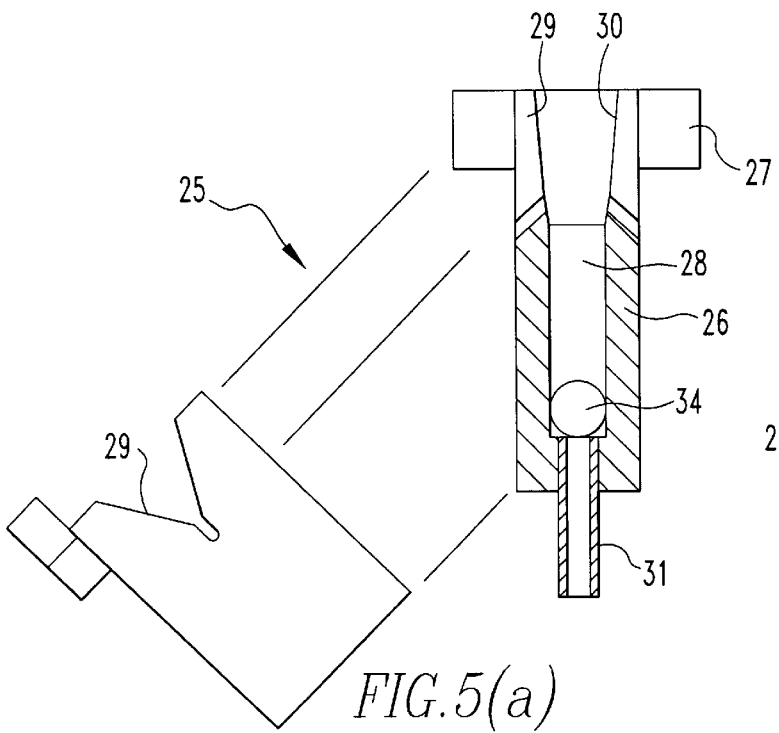
FIG. 5(a) is a front elevation partially in cross section of a wash fluid-ejecting block used in the pipette-washing device shown in FIG. 2.
Figure 5C:
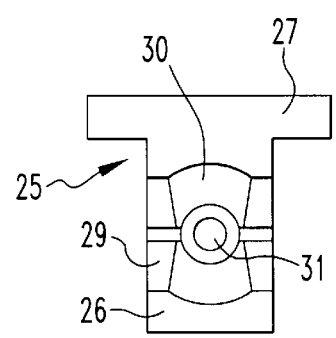
FIG. 5(c) is a plan view of the wash fluid-ejecting block shown in FIG. 5(a)

FIG. 2 is a front elevation of the pipette-washing device according to the present invention. FIG. 3 is a side elevation partially in cross section of the pipette-washing device. FIG. 4 is a plan view of the pipette-washing device. In these figures, the pipette-washing device, generally indicated by reference numeral 16, comprises a potlike container 24 of rectangular cross section. This container 24 is open on its top side. A wash water-ejecting block 25 is mounted on top of the container 24 and located under a passage through which the pipette moves. The wash water-ejecting block 25 is composed of a body 26 in the form of a block and an attachment portion 27. The body 26 of the block is provided with a vertical hole 28 extending longitudinally of the body 26. This vertical hole 28 forms a passage for the wash water. A V-groove 29 is formed in the top surface of the body 26 and extends horizontally through the body. The vertical hole 28 opens into the bottom of this V-groove 29. The side walls defining the V-groove 29 are provided with arc-shaped recesses 30 having a diameter substantially equal to the diameter of the vertical hole 28.

A communication tube 31 is fitted at the lower end of the vertical hole 28. This communication tube 31 is connected to a wash water reservoir (not shown) via all of a water supply tube 32, a normally closed solenoid valve 33, and a wash water supply pump (not shown).

A lateral hole 34 having the same diameter as that of the vertical hole 28 is formed in the body 26 and intersects with the vertical hole 28 at a location slightly higher than the top end of the communication tube 31. This lateral hole 34 opens into the atmosphere through one side wall of the body 26.

As shown in FIGS. 2–4, the attachment portion 27 of the wash water-ejecting block 25 is screwed or otherwise mounted to a mounted portion 36 on the top outer surface of the container 24 via a bracket 35. This ejecting block 25 is so mounted that the body 26 is almost fully nested within the container 24 as shown in FIG. 3 and that the block 25 is inclined at an angle to the vertical within a plane in which the V-groove 29 extends, i.e., within the plane of FIG. 2. When the sampling pipette 14 is rotated from the dilution turntable 6 to the reaction turntable 12 or vice versa, the front end of the sampling pipette 14 passes through the V-groove 29.

A draining tube 37 is connected with the bottom of the container 24 and also with the draining tank (not shown). The operation of the turntable 4, the pipettes 13, 14, 17, 18, the stirring devices 15, 19, 20, the washing devices 16, 23, the detector, the solenoid valve, and the various pumps is under control of a control unit (not shown) consisting of a computer or the like.

Figure 6:
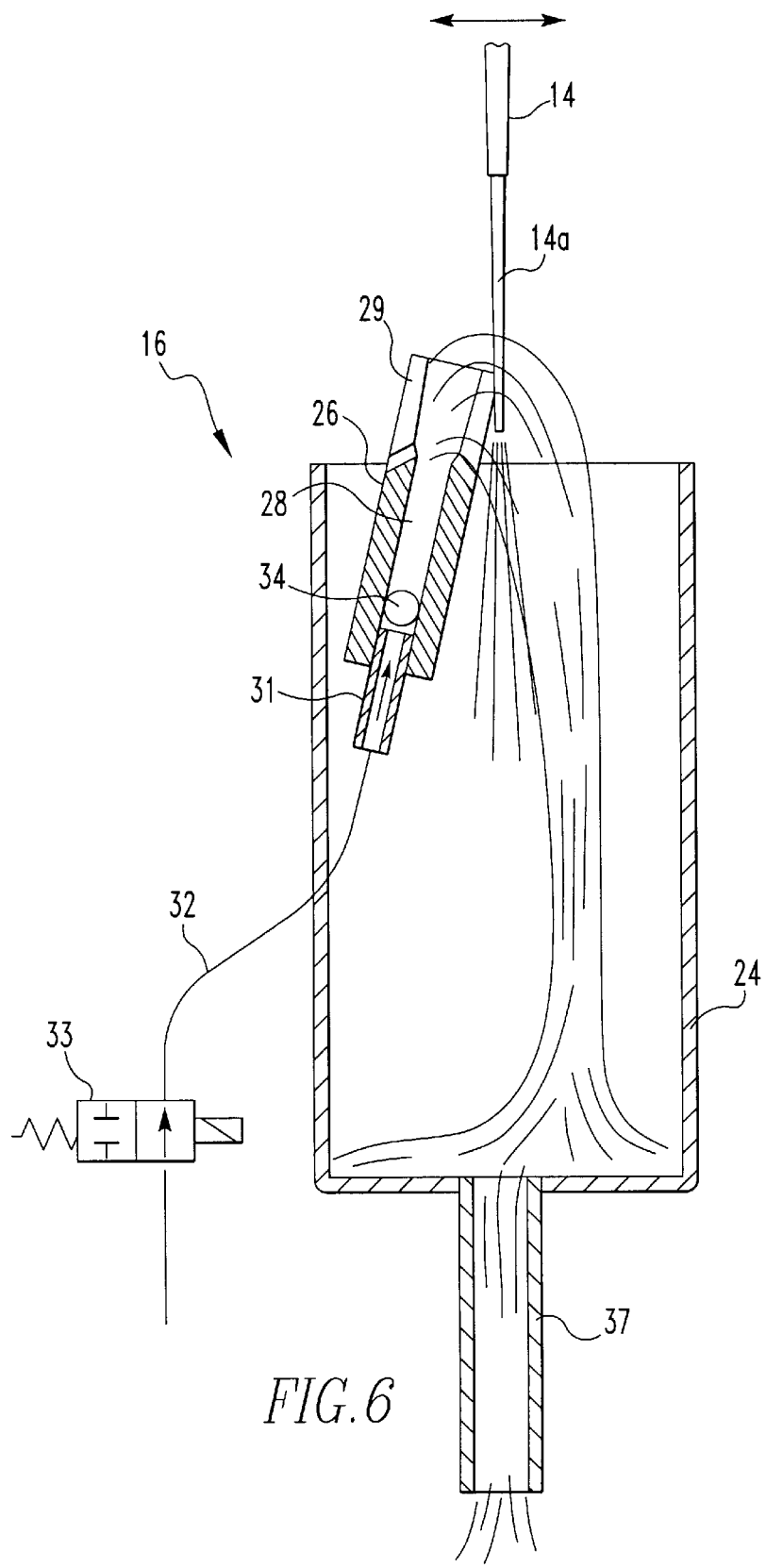
FIG. 6 is a vertical cross section of the pipette-washing device shown in FIG. 2, and in which wash water is being supplied.
Figure 7:
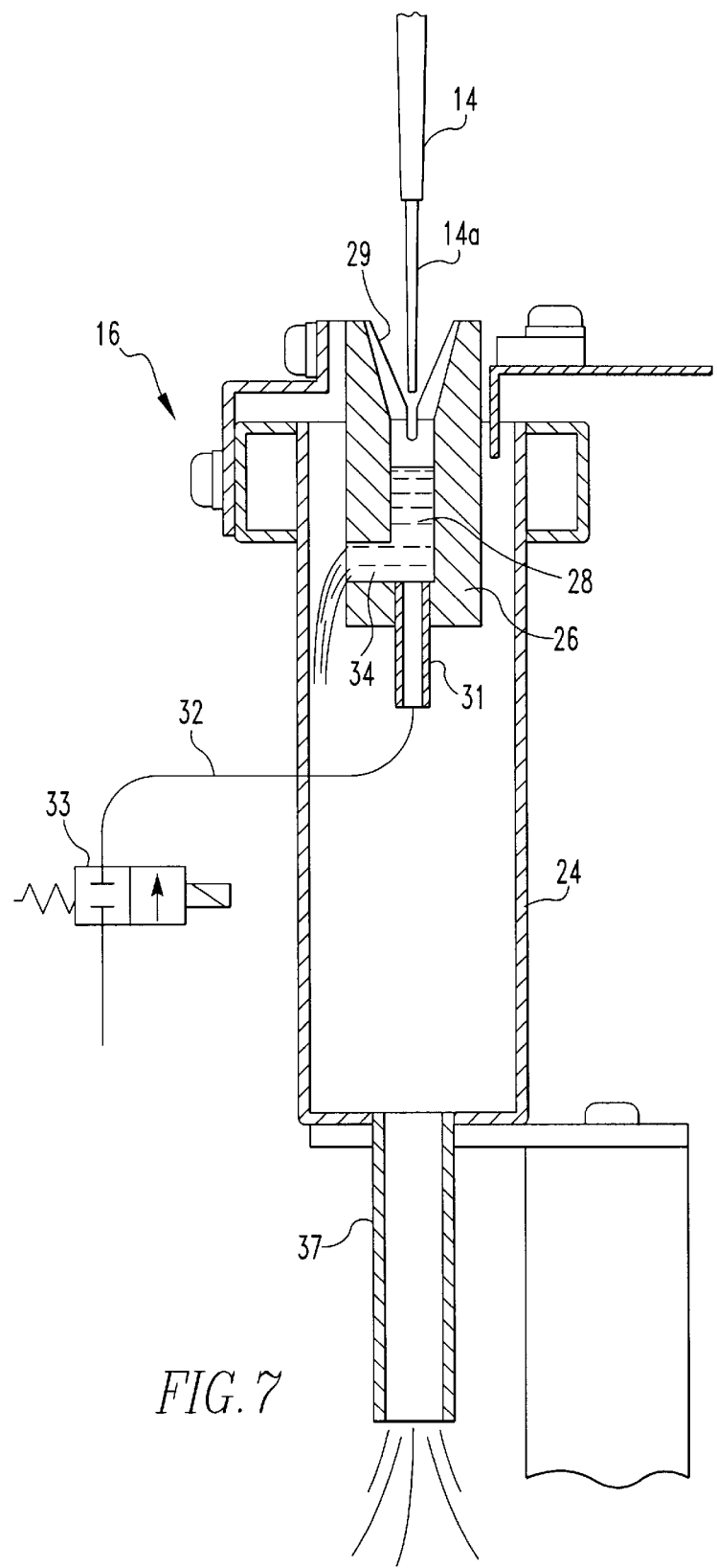
FIG. 7 is a vertical cross section similar to FIG. 6, but in which wash water is being drained away.

The present pipette-washing device 16 constructed in this way activates the solenoid valve 33 to open it and, at the same time, drives a wash water supply pump (not shown) to supply a wash water to the wash water-ejecting block 25, as shown in FIG. 6. The wash water then flows upward through the vertical hole 28 in the block 25 and reaches the V-groove 29, whence the water leaves one side of the block 25. The water then falls into the container 24, passes through the draining tube, and is drained off into the draining tank (not shown).

The flow rate of the wash water is so set that the water flowing out of the V-groove 29 constantly forms a raised portion higher than the top surface of the body outside the body as shown in FIG. 6. The wash water entering the vertical hole 28 from the communication tube 31 flows upward at a given flow velocity, thus producing a negative pressure inside the lateral hole 34. This prevents the wash water from leaking out through the lateral hole 34.

Under this condition, a front end portion 14a of the sampling pipette 14 is advanced into the raised portion of the wash water and brought to a stop at the illustrated position where the water discharged from the sampling pipette 14 does not collide against the wash water-ejecting block 25. In the present invention, the ejecting block 25 is mounted at an angle and so the pipette can be halted at a position where the wash water discharged from the pipette is not splashed onto the wash water-ejecting block but the wash water flowing out of the block is splashed against the front end of the pipette.

During the halt at this location, the sample and diluent adhering to the outer surface of the front end portion 14a of the sampling pipette 14 are washed away by the wash water. The interior of the sampling pipette 14 can be cleaned by aspirating a given amount of wash water into the sampling pipette 14 and discharging the water. The wash water ejected from the sampling pipette 14 falls into the container 24 without colliding against the wash water-ejecting block 25, and is discharged from the draining tube 37, in the same way as in the processing described above.

When the washing of the inside and outside of the sampling pipette 14 is complete, the solenoid valve 33 is closed and, at the same time, the operation of the wash water supply pump is stopped. Thus, the supply of the wash water is stopped. Then, the wash water located inside the vertical hole and over the lateral hole 34 flows through the lateral hole 34 by its own weight and is drained off into the container 24. As a result, the surface of the wash water raised high because the water is gushing out of the ejecting block 25 drops slowly at an appropriate time constant. As the wash water in which the front end portion of the pipette is immersed drops slowly in level in this way, the surface tension of the wash water carries away the wash water adhering to the outer surface of the front end portion, together with the water surface. In consequence, little wash water is left on the surface of the pipette after the water surface has passed. The amount of the wash water remaining on the surface of the outer surface of the front end portion of the pipette is much smaller than where splashing of wash water on the outer surface of the pipette is stopped momentarily.

In this way, with the pipette-washing device in accordance with the present invention, the outer surface of the aspirating portion 14a of the sampling pipette 14 and the interior of the sampling pipette 14 are simultaneously washed. Therefore, the sampling pipette 14 is cleansed reliably and efficiently. Consequently, the wash time can be shortened.

Furthermore, the wash water is drained away well and so almost no wash water is left on the sampling pipette 14. This assures that the sampling pipette 14 is washed more effectively.

It is to be understood that the arc-shaped recesses 30 in the side walls defining the groove 29 are not essential to the present invention. The recesses 30 may be omitted, and the side walls defining the groove 29 may be shaped into simple flat planes. In addition, the groove 29 is not always required to have a V-shaped cross section. The groove may also have a U-shaped cross section, a rectangular cross section, or a trapezoidal cross section as long as the groove has a large opening on its top side.

In the above embodiment, the device for washing the sampling pipette 14 has been described. The invention may also be applied to pipette-washing devices for washing the sample-diluting pipette 13 and the reagent pipettes 17, 18.

Moreover, the lateral hole 34 formed in the body 26 of the wash water-ejecting block 25 is not always required to intersect the vertical hole 28 at right angles. The lateral hole 34 may also be tilted downward outwardly of the body 26 so as to intersect the vertical hole 29 obliquely.

What is claimed is:

1. A pipette-washing device connectable to a wash fluid supply for washing a pipette that aspirates a sample or reagent to be handled by an automatic biochemical analyzer and conveys the aspirated sample or reagent into another location, said pipette-washing device comprising:

a wash fluid-ejecting block having a top end, a bottom end, and a top surface, said wash fluid-ejecting block being mounted under a path through which said pipette having a front end moves, said front end of said pipette describing a trajectory, said wash fluid-ejecting block acting to eject a wash fluid toward said pipette;

a valve for controlling supply of said wash fluid from said wash fluid supply to said wash fluid-ejecting block;

said wash fluid-ejecting block comprising a body in the form of a block said body having an opening in its top surface, said opening facing the front end of said pipette;

a wash fluid channel extending generally vertically in said body, said wash fluid channel having a top and bottom end, said wash fluid channel connected with a generally vertical wash fluid supply passage at the bottom end of said block;

an upwardly spreading groove formed in the top surface of said body and extending along the trajectory of the front end of said pipette, said front end of said pipette passing through said groove during generally horizontal movement of said pipette, said groove being connected with said wash fluid channel;

a draining channel formed in said body and opening into the atmosphere through one side wall of said body, said wash fluid channel being connected near its lower end with said draining channel; and said wash fluid-ejecting block being inclined at an angle to a vertical line within a plane in which said groove extends.

2. The pipette-washing device of claim 1, wherein said groove has a V-shaped, U-shaped, or other upwardly spreading cross section.

3. The pipette-washing device of claim 1, wherein said wash fluid supply means supplies said wash fluid at such a flow velocity that the wash fluid is ejected upwardly from said opening located over said wash fluid channel to a height that is constantly higher than the top surface of said body.

4. The pipette-washing device of claim 1, wherein said pipette is halted at a halt position where the wash fluid discharged from said pipette is not splashed onto said wash fluid-ejecting block but the wash fluid flowing out of said wash fluid-ejecting block is splashed against the front end of said pipette.

5. The pipette-washing device of claim 4, further comprising a container that receives the wash fluid discharged from all of said groove, said draining channel, and said pipette.

6. The pipette-washing device of claim 4, wherein said valve is opened before said pipette reaches said halt position and is closed before washing of said pipette is complete and said pipette is moved.

7. A device for washing a pipette comprising:

a wash fluid-ejecting block mounted under a path through which said pipette moves in an established trajectory, said wash fluid-ejecting block acting to eject a wash fluid toward said pipette;

a valve for controlling supply of said wash fluid from a wash fluid supply to said wash fluid-ejecting block;

an upwardly spreading groove formed in the top surface of said fluid-ejecting block extending along the trajectory of said pipette, said groove wide enough to permit the pipette to pass through said groove during generally horizontal movement of said pipette, said wash fluid-ejecting block being inclined at an angle generally to a vertical within a plane in which the groove extends such that the pipette can be stopped adjacent the fluid-ejecting block and flushed without contaminating the fluid-ejecting block and while was fluid ejected toward the pipette cleans the exterior of the pipette and such that when the valve controlling said wash fluid is shut off the wash fluid in which the pipette is immersed drops slowly enough for surface tension of the wash fluid to carry away fluid adhering to the pipette.

* * * * *

UNITED STATES PATENT AND TRADEMARK OFFICE
CERTIFICATE OF CORRECTION

PATENT NO.   : 6,003,531
DATED        : December 21, 1999
INVENTOR(S)  : Akio Kimura et al.

It is certified that error appears in the above-identified patent and that said Letters Patent is hereby corrected as shown below:

Title Page, [57] ABSTRACT, line 4, "toward pipette" should read
    --toward the pipette--.

Column 1 Line 16 "aliquots or sample" should read --aliquots
    of sample--.

Column 3 Line 44 "to drawn" should read --to draw--.

Column 4 Line 27 "held in other" should read --held in the other--.

Column 8 Line 48, Claim 7, "was fluid" should read --wash fluid--.

Signed and Sealed this

Eighth Day of August, 2000

Q. TODD DICKINSON

*Attest:*

*Attesting Officer*          *Director of Patents and Trademarks*